United States Patent [19]

Wei et al.

[11] Patent Number: 5,344,773
[45] Date of Patent: Sep. 6, 1994

[54] HUMAN UTERINE TISSUE PLASMINOGEN ACTIVATOR PRODUCED BY RECOMBINANT DNA

[75] Inventors: Cha-Mer Wei, Seattle, Wash.; Nancy Hsiung, Wellesley; Vermuri B. Reddy, Framingham, both of Mass.; Jeffrey F. Lemontt, West Newton; William Dackowski, Ashland, both of Mass.; Richard Douglas, Southboro; Edward S. Cole, Mendon, both of Mass.; Richard D. Purcell, Jr., Newton; David Tai-Yui Lau, Marlboro, both of Mass.

[73] Assignee: Genzyme Corporation, Cambridge, Mass.

[21] Appl. No.: 782,686

[22] Filed: Oct. 1, 1985

Related U.S. Application Data

[60] Continuation-in-part of Ser. No. 656,770, Oct. 1, 1984, abandoned.

[51] Int. Cl.$^5$ ............ C12N 9/64; C12N 15/58; A61K 37/547
[52] U.S. Cl. .................. 435/226; 435/212; 435/240.2; 435/254.21; 435/320.1; 536/23.2; 536/23.5
[58] Field of Search .......... 435/172.3, 320, 240.2, 435/253, 255, 212, 172.1, 226, 320.1, ; 935/27, 28, 29, 32, 14, 69, 70, 72, 50; 536/27, 23.5, 23.2

[56] References Cited

U.S. PATENT DOCUMENTS

| 4,370,417 | 1/1983 | Hung | 435/215 |
| 4,419,446 | 12/1983 | Howley | 435/172.3 |

FOREIGN PATENT DOCUMENTS

| 35719 | 9/1984 | Australia . | |
| 0093619 | 9/1983 | European Pat. Off. | 435/212 |
| 0117059 | 8/1984 | European Pat. Off. | 435/212 |
| 227462 | 10/1987 | European Pat. Off. . | |
| 225286 | 1/1988 | European Pat. Off. . | |
| 238304 | 1/1988 | European Pat. Off. . | |
| 8401786 | 5/1984 | PCT Int'l Appl. | 435/212 |

OTHER PUBLICATIONS

Rijken, D. et al., *J. Biol. Chem.*, vol. 256, pp. 7035–7041, 1981.
Pohl, G. et al., *Biochemistry*, vol. 23, pp. 3701–3707, Jul. 1984.
Zoller, M. et al., *Nucleic Acids Research*, vol. 10, pp. 6487–6500, 1982.
Berman, P. et al., *Trends in Biotechnology*, vol. 3, pp. 51–53, Feb., 1985.
Pennica, D. et al., *Nature*, vol. 301, pp. 214–221, 1983.
Lemontt, J. et al., *DNA*, vol. 4, pp. 419–428, Dec. 1985.
Pohl, G. et al., *FEBS*, vol. 168, pp. 29–32, Mar. 1984.
Vehar, G. A. et al., Biotechnology, vol. 2, Dec. 1984, pp. 1051–1057, "Characterization Studies on Human Melanoma Cell Tissue Plasminogen Activator".
Little et al., *Biochemistry*, vol. 23, pp. 6191–6195, Dec. 4, 1984.
Van Zonneveld, et al., *J. Cell. Biochemistry*, pp. 169–178, 1986.
Tor Ny et al., *Proc. Natl. Acad. Sci.*, vol. 81, pp. 5355–5359, (Sep. 1984).
Rijken (1979) Biochem. Biophys. Acta. 580, 140.

*Primary Examiner*—Robert J. Hill, Jr.
*Assistant Examiner*—Marianne Porta Allen
*Attorney, Agent, or Firm*—Fish & Richardson

[57] ABSTRACT

A replicable expression vector capable, in a transformed host mammallian cell, of expressing a DNA sequence encoding active human TPA which, when expressed in the host cell, yields active TPA which lacks one or more of the TPA-bound N-linked carbohydrate moieties of naturally occurring human TPA.

21 Claims, 10 Drawing Sheets

FIG 1A

```
ctgtgaagcaatc ATG GAT GCA ATG AAG AGA GGG CTC TGC TGT GTG CTG CTG CTG TGT GGA GCA GTC TTC
              met asp ala met lys arg gly leu cys cys val leu leu leu cys gly ala val phe
              -38                      -30                            -20
                                    100
GTT TCG CCC AGC CAG GAA ATC CAT GCC CGA TTC AGA AGA|GGA GCC AGA|TCT TAC CAA|GTG ATC TGC AGA
val ser pro ser gln glu ile his ala arg phe arg arg|gly ala arg|ser tyr gln|VAL Ile Cys Arg
                              -10                                            1
                                                                                  200
GAT GAA AAA ACG CAG ATG ATA TAC CAG CAA CAT CAG TCA TGG CTG CGC CCT GTG CTC AGA AGC AAC CGG
Asp Glu Lys Thr Gln Met Ile Tyr Gln Gln His Gln Ser Trp Leu Arg Pro Val Leu Arg Ser Asn Arg
                    10                                      20

GTG GAA TAT TGC TGG TGC AAC AGT GGC AGG GCA CAG TGC CAC TCA GTG CCT GTC AAA AGT TGC AGC GAG
Val Glu Tyr Cys Trp Cys Asn Ser Gly Arg Ala Gln Cys His Ser Val Pro Val Lys Ser Cys Ser Glu
            30                              40                                          50
                    300
CCA AGG TGT TTC AAC GGG GGC ACC TGC CAG CAG GCC CTG TAC TTC TCA GAT TTC GTG TGC CAG TGC CCC
Pro Arg Cys Phe Asn Gly Gly Thr Cys Gln Gln Ala Leu Tyr Phe Ser Asp Phe Val Cys Gln Cys Pro
                            60                                              70
                                                                400
GAA GGA TTT GCT GGG AAG TGC TGT GAA ATA GAT ACC AGG GCC ACG TGC TAC GAG GAC CAG GGC ATC AGC
Glu Gly Phe Ala Gly Lys Cys Cys Glu Ile Asp Thr Arg Ala Thr Cys Tyr Glu Asp Gln Gly Ile Ser
                    80                                              90
                                                                    CHO
TAC AGG GGC ACG TGG AGC ACA GCG GAG AGT GGC GCC GAG TGC ACC AAC TGG AAC AGC AGC GCG TTG GCC
Tyr Arg Gly Thr Trp Ser Thr Ala Glu Ser Gly Ala Glu Cys Thr Asn Trp Asn Ser Ser Ala Leu Ala
            100                                     110
            500
CAG AAG CCC TAC AGC GGG CGG AGG CCA GAC GCC ATC AGG CTG GGC CTG GGG AAC CAC AAC TAC TGC AGA
Gln Lys Pro Tyr Ser Gly Arg Arg Pro Asp Ala Ile Arg Leu Gly Leu Gly Asn His Asn Tyr Cys Arg
120                                     130                                         140
                                        600
AAC CCA GAT CGA GAC TCA AAG CCC TGG TGC TAC GTC TTT AAG GCG GGG AAG TAC AGC TCA GAG TTC TGC
Asn Pro Asp Arg Asp Ser Lys Pro Trp Cys Tyr Val Phe Lys Ala Gly Lys Tyr Ser Ser Glu Phe Cys
                        150                                 160
                                                CHO
AGC ACC CCT GCC TGC TCT GAG GGA AAC AGT GAC TGC TAC TTT GGG AAT GGG TCA GCC TAC CGT GGC ACG
Ser Thr Pro Ala Cys Ser Glu Gly Asn Ser Asp Cys Tyr Phe Gly Asn Gly Ser Ala Tyr Arg Gly Thr
                170                                     180
        700
CAC AGC CTC ACC GAG TCG GGT GCC TCC TGC CTC CCG TGG AAT TCC ATG ATC CTG ATA GGC AAG GTT TAC
His Ser Leu Thr Glu Ser Gly Ala Ser Cys Leu Pro Trp Asn Ser Met Ile Leu Ile Gly Lys Val Tyr
190                                     200                                         210
```

FIG 1B

```
          CHO                                                800
ACA GCA CAG AAC CCC AGT GCC CAG GCA CTG GGC CTG GGC AAA CAT AAT TAC TGC CGG AAT CCT GAT GGG
Thr Ala Gln Asn Pro Ser Ala Gln Ala Leu Gly Leu Gly Lys His Asn Tyr Cys Arg Asn Pro Asp Gly
                        220                                         230

GAT GCC AAG CCC TGG TGC CAC GTG CTG AAG AAC CGC AGG CTG ACG TGG GAG TAC TGT GAT GTG CCC TCC
Asp Ala Lys Pro Trp Cys His Val Leu Lys Asn Arg Arg Leu Thr Trp Glu Tyr Cys Asp Val Pro Ser
                    240                                 250
900                                                        ↓
TGC TCC ACC TGC GGC CTG AGA CAG TAC AGC CAG CCT CAG TTT CGC ATC AAA GGA GGG CTC TTC GCC GAC
Cys Ser Thr Cys Gly Leu Arg Gln Tyr Ser Gln Pro Gln Phe Arg Ile Lys Gly Gly Leu Phe Ala Asp
            260                             270                             280
                                1000
ATC GCC TCC CAC CCC TGG CAG GCT GCC ATC TTT GCC AAG CAC AGG AGG TCG CCC GGA GAG CGG TTC CTG
Ile Ala Ser His Pro Trp Gln Ala Ala Ile Phe Ala Lys His Arg Arg Ser Pro Gly Glu Arg Phe Leu
                            290                                         300
                                                                            1100
TGC GGG GGC ATA CTC ATC AGC TCC TGC TGG ATT CTC TCT GCC GCC CAC TGC TTC CAG GAG AGG TTT CCG
Cys Gly Gly Ile Leu Ile Ser Ser Cys Trp Ile Leu Ser Ala Ala His Cys Phe Gln Glu Arg Phe Pro
                        310                             320

CCC CAC CAC CTG ACG GTG ATC TTG GGC AGA ACA TAC CGG GTG GTC CCT GGC GAG GAG GAG CAG AAA TTT
Pro His His Leu Thr Val Ile Leu Gly Arg Thr Tyr Arg Val Val Pro Gly Glu Glu Glu Gln Lys Phe
                330                                 340
                                1200
GAA GTC GAA AAA TAC ATT GTC CAT AAG GAA TTC GAT GAT GAC ACT TAC GAC AAT GAC ATT GCG CTG CTG
Glu Val Glu Lys Tyr Ile Val His Lys Glu Phe Asp Asp Asp Thr Tyr Asp Asn Asp Ile Ala Leu Leu
350                                     360                                     370
                                                                1300
CAG CTG AAA TCG GAT TCG TCC CGC TGT GCC CAG GAG AGC AGC GTG GTC CGC ACT GTG TGC CTT CCC CCG
Gln Leu Lys Ser Asp Ser Ser Arg Cys Ala Gln Glu Ser Ser Val Val Arg Thr Val Cys Leu Pro Pro
                            380                                         390

GCG GAC CTG CAG CTG CCG GAC TGG ACG GAG TGT GAG CTC TCC GGC TAC GGC AAG CAT GAG GCC TTG TCT
Ala Asp Leu Gln Leu Pro Asp Trp Thr Glu Cys Glu Leu Ser Gly Tyr Gly Lys His Glu Ala Leu Ser
                    400                                 410
                        1400
CCT TTC TAT TCG GAG CGG CTG AAG GAG GCT CAT GTC AGA CTG TAC CCA TCC AGC CGC TGC ACA TCA CAA
Pro Phe Tyr Ser Glu Arg Leu Lys Glu Ala His Val Arg Leu Tyr Pro Ser Ser Arg Cys Thr Ser Gln
    420                                     430                                     440
            CHO                                         1500
CAT TTA CTT AAC AGA ACA GTC ACC GAC AAC ATG CTG TGT GCT GGA GAC ACT CGG AGC GGC GGG CCC CAG
His Leu Leu Asn Arg Thr Val Thr Asp Asn Met Leu Cys Ala Gly Asp Thr Arg Ser Gly Gly Pro Gln
                        450                                         460

GCA AAC TTG CAC GAC GCC TGC CAG GGC GAT TCG GGA GGC CCC CTG GTG TGT CTG AAC GAT GGC CGC ATG
Ala Asn Leu His Asp Ala Cys Gln Gly Asp Ser Gly Gly Pro Leu Val Cys Leu Asn Asp Gly Arg Met
                        470                                         480
        1600                                                                        A
ACT TTG GTG GGC ATC ATC AGC TGG GGC CTG GGC TGT GGA CAG AAG GAT GTC CCG GGT GTG TAC ACC AAG
Thr Leu Val Gly Ile Ile Ser Trp Gly Leu Gly Cys Gly Gln Lys Asp Val Pro Gly Val Tyr Thr Lys
        490                             500                                         510
```

FIG 1C

```
                                                        1700
GTT ACC AAC TAC CTA GAC TGG ATT CGT GAC AAC ATG CGA CCG TGA    CCAGGAACAC CCGACTCCTC
Val Thr Asn Tyr Leu Asp Trp Ile Arg Asp Asn Met Arg Pro ***
                                                520
                                                                        1800
AAAAGCAAAT GAGATCCCGC CTCTTCTTCT TCAGAAAACA CTGCAAAGGC GCAGTGCTTC TCTACAGACT TCTCCAGACC
                                     G

CACCACACCG CAGAAGCGGG ACGAGACCCT ACAGGAGAGG GAAGAGTGCA TTTTCCCAGA TACTTCCCAT TTTGGAAGTT
                 1900
TTCAGGACTT GGTCTGATTT CAGGATACTC TGTCAGATGG GAAGACATGA ATGCACACTA GCCTCTCCAG GAATGCCTCC

2000
TCCCTGGGCA GAAATGCCA TGCCACCCTG TTTTCAGCTA AAGCCCAACC TCCTGACCTG TCACCGTGAG CAGCTTTGGA
              G                        X
                                                             2100
AACAGGACCA CAAAAATGAA AGCATGTCTC AATAGTAAAA GATAACAAGA TCTTTCAGGA AAGACGGATT GCATTAGAAA
                                             X    /GA
                                                                              2200
TAGACAGTAT ATTTATAGTC ACAAGAGCCC AGCAGGGCTC AAAGTTGGGG CAGGCTGGCT GGCCCGTCAT GTTCCTCAAA
                           G

AGCACCCTTG ACGTCAAGTC TCCTTCCCCT TTCCCCACTC CCTGGCTCTC AGAAGGTATT CCTTTTGTGT ACAGTGTGTA
   G                                                                         A
                 2300
AAGTGTAAAT CCTTTTTCTT TATAAACTTT AGAGTAGCAT GAGAGAATTG TATCATTTGA ACAACTAGGC TTCAGCATAT
                 2400
TTATAGCAAT CCATGTTAGT TTTTACTTTC TGTTGCCACA ACCCTGTTTT ATACTGTACT TAATAAATTC AGATATATTT
       G      /C                 C                              C                G

TTCACAGTTT TTCCA
/T
```

HUMAN UTERINE TISSUE PLASMINOGEN ACTIVATOR PRODUCED BY RECOMBINANT DNA

BACKGROUND OF THE INVENTION

This invention relates to the use of recombinant DNA techniques to produce therapeutic proteins, in particular to the use of such techniques to produce the protein human uterine tissue plasminogen activator (uTPA).

Rijken et al. (1979) Biochim. Biophys. Acta 580, 140 describes the partial purification, from human uterine tissue, of uTPA, a single chain zymogenic enzyme activatable by plasmin in blood to a 2-chain form capable of dissolving fibrin clots. uTPA is thus undoubtedly useful as a therapeutic composition for dissolving clots in patients suffering from a variety of vascular diseases, particularly myocardial infarctions resulting in clots in and around the heart.

Recombinant DNA techniques have previously been used to obtain mRNA from a line of cancer cells (Bowes melanoma cells) and the mRNA used to produce cDNA encoding Bowes TPA, as described in Goeddel et al. European Pat. Appln. No. 0093619.

SUMMARY OF THE INVENTION

In general, the invention features a cDNA sequence encoding active human uterine TPA.

In another aspect, the invention features a replicable expression vector capable, in a transformed host cell, of expressing a DNA sequence encoding active human uterine TPA, and a host cell, e.g., a yeast or mammalian cell, transformed with the vector.

The cultured transformed cells are used to produce uTPA, which is free of other non-human proteins, and which can be purified to be at least 97% free, by weight, from non-uTPA proteins.

The uTPA is purified from the mammalian cell culture medium, or, in the case of yeast, from an extract of cellular material, in a process optionally including a first liquid/liquid phase extraction step to remove a portion of the non-uTPA protein from the medium to yield a composition having an increased uTPA specific activity.

The liquid/liquid phase extraction step is carried out by mixing the culture medium or extract with two different water-soluble, polymeric compounds to form a two-phase mixture in which at least 65%, by weight, of the uTPA is present in one phase and at least 40%, by volume, of the water in the medium or extract is present in the other phase. Purification and concentration can also include the steps of ultrafiltration and/or hydrophobic affinity chromatography. Preferably the method further includes an affinity chromatography step by which uTPA is bound to anti-TPA antibody.

The uTPA of the invention is encoded by expression vectors which, because of the origin of the gene (normal human uterine tissue), simulate normal biosynthesis of uTPA in humans (including, probably, glycosylation patterns, when eukaryotic host cells are used), so that the protein product will behave naturally in human patients.

The invention also provides partially or non-glycosylated TPA's produced in eukaryotic cells; these modified TPA's advantageously provide longer half-lives.

We now describe preferred embodiments of the invention.

DESCRIPTION OF THE PREFERRED EMBODIMENTS

The drawings will first be described.

Drawings

FIG. 1A–C is a diagrammatic representation of the base sequence of the human uterine TPA gene, including flanking regions; the differences between the uterine TPA gene and the Bowes melanoma TPA gene are indicated.

SYNTHESIS OF HUMAN UTERINE TPA cDNA

The cDNA encoding human uterine TPA was produced and cloned according to the following main steps:

1) total mRNA was isolated from human uterine tissue;
2) uTPA mRNA was enriched from total mRNA;
3) cDNA was synthesized from theta mRNA to give a 3' and a 5' cDNA sequence;
4) the 5' and 3' cDNA sequences were combined to give the complete cDNA sequence in an intermediate plasmid vector.

Isolation of uTPA mRNA

The mRNA from the human uterine tissue was isolated as follows. About 30 g of human uterine tissue in 40 ml of guanidine thiocyanate solution containing 4M guanidine thiocyanate, 1M 2-mercaptoethanol, 50 mM sodium acetate (pH 5.0) and 1 mM EDTA were ground in a tissue homogenizer. One g CsCl per ml of homogenate was then added, and the homogenate centrifuged at 3000 rpm for 10 minutes. The supernatant was layered on 15 ml of "CsCl cushion" containing 50 mM sodium acetate (pH 5.0), 1 mM EDTA, and 1.592 g CsCl per ml of solvent in 50 ml tubes and centrifuged at 45,000 rpm at 20° C. for 24 hours. The white band containing RNA was collected, the CsCl solution diluted 3-fold with water, and RNA precipitated by the addition of 2 volumes of ethanol at −20° C. The precipitate was collected by centrifugation. Any CsCl contamination was removed by repeating the solubilization and precipitation procedure. About 11 mg of purified RNA was recovered.

The purified RNA was applied to are affinity column containing (10 ml of oligo-dT cellulose in high salt buffer (10 mM Tris (pH 8.0), 0.5M NaCl, and 0.2% sodium dodecylsulfate) and concentrated by ethanol precipitation to yield 300ug concentrated RNA. The RNA was dissolved in 200 µl of 0.1M TrisHCl (pH 7.5), 1 mM EDTA, 1% sodium dodecylsulfate, and 50% formamide in SW41 tubes. The tubes were centrifuged at 35,000 rpm at 15° C. for 16 hours. Fractions were collected and the size of the RNA in each fraction was determined by internal $^3$H-labeled 4S, 18S, and 28S markers.

The fractions containing TPA mRNA were identified by Northern blotting analysis using a $^{32}$P labeled probe and pooled together. The mRNA was recovered from the gradient by dilution with an equal volume of 0.4M NaOAc, pH 5, and precipitated with ethanol in a volume 2.5 times that of the diluted gradient solution. Any formamide which still contaminated the recovered RNA was removed by repeated solubilization and precipitation.

Production of a 3' Sequence of uTPA cDNA

The first strand of uTPA cDNA was produced from isolated mRNA as follows. In a total volume of 50 ul containing 50 mM TrisHCl, pH 8.3, 50 mM KCl, 8 mM MgCl$_2$, 1 mM each of dATP, dCTP, dGTP and dTTP, 25 ug/ml oligo-dT$_{12-18}$, 50 ug/ml actinomycin D, 30 mM. 2-mercaptoethanol, 0.5 mCl/ml [d$^{32}$P]dcTP, 50 units of RNA sin, and 40 units of AMV reverse transcriptase, the RNA was incubated at 37° C. for 1 hour and stopped by addition of 20 mM EDTA. The reaction mixture was then applied to a Sephadex G-100 column equilibrated with 10 mM Tris-HCl (pH 8.0), 1 mM EDTA, and 0.1% sodium dodecylsulfate and prechromatographed with 50 ug E. coli tRNA.

The fractions containing the mRNA-cDNA hybrid were pooled and precipitated by the addition of ethanol. The recovered hybrid was treated with 0.5N NaOH at 37° C. for several hours, neutralized with glacial acetic acid, and precipitated with ethanol.

Nucleotide triphosphates were removed by high saltethanol precipitation in the following manner. The DNA was first dissolved in 20 to 50 ul of water and an equal volume of 4M ammonium acetate was added. Two volumes of ethanol were then added and kept at −70° C. overnight. The solution was allowed to return to room temperature and centrifuged to pellet the DNA. This procedure was repeated two more times, and the pellet was then washed once with 70% ethanol, yielding a purified first strand of cDNA corresponding to a large portion of the 3' end of the TPA gene.

The first strand of cDNA was used for or second strand cDNA synthesis in a total volume of 100 ul containing 50mM HEPES buffer (pH 6.9), 10 mM MgCl$_2$, 2 mM DTT, 70 mM KCl, 0.5 mM each of dATP, dCTP, dGTP, dTTP. To the mixture, 20 units of DNA polymerase-Klenow fragment were added at 15° C. for 20 hours. The DNA was extracted with a 1:1, v/v, mixture of phenol and chloroform and precipitated with ethanol.

The double-stranded cDNA was treated with S1 nuclease to remove hairpin structures in a total volume of 100 ul containing 30 mM NaOAc (pH 4.5), 0.3M NaCl, 4.5 mM ZnCl, and 50 units of S1 nuclease at room temperature for 30 minutes. The reaction was stopped by addition of EDTA and 1M TrisHCl, pH 8.0, to give final concentrations of 10 mM and 0.1M, respectively. The DNA was purified by phenol-chloroform extraction and repeated ethanol precipitation in the presence of high salt as described previously.

The purified double-stranded cDNA sequence was cloned as follows. The double-stranded cDNA was first tailed with oligo-dC in a reaction volume of 100 ul containing 60 mM cacodylate-0.14M Tris (pH 7.6), 1 mM dithiothreitol, 0.1 mM dCTP, and 0.2 uCi/ul [$^3$H]dCTP. Ten mM CaCl$_2$ was added last to a final concentration of 1 mM and 50 units of terminal deoxytransferase were added at 15° C. over 10 minutes. The reaction was stopped by the addition of EDTA to 10 mM and sodium dodecylsulfate to 0.1% and diluted two-fold with water. The reaction mixture was then subjected to gel electrophoresis in agarose, and the cDNA of 500 bp or longer recovered from the gel.

The oligo-dC tailed cDNA was annealed to oligo-dG tailed pBR322 DNA which had been linearized with PstI in a total volume of 0.5 ml containing 15 mM TrisHCl (pH 7.5), 150 mM NaCl, and 1 mM EDTA at 65° C. for 10 minutes, then at 42° C. for 2 hours. The annealed DNA was used to transform 2.5 ml competent E. coli (MC1061) cells which had been pretreated with CaCl$_2$ and kept frozen. The mixture of cells and DNA was kept on ice for 20 minutes, heat shocked for 7 minutes at 37° C., then incubated with 20 volumes of L broth at 37° C. for 45 minutes and plated on L-plates containing 15 ug/ml tetracycline.

The recombinant clones were transferred to nitrocellulose filters, and one set of filters was placed on the tetracycline plates for storage of viable clones. A second set of filters containing replicate recombinant clones was placed on chloramphenicol plates at 37° C. overnight for plasmid amplification. Filters were processed to expose the DNA. Prehybridization of filters was carried out in a solution containing 50% formamide, 3XSSC, 5X Denhart's, 0.1% sodium dodecylsulfate, and 100 ug/ml E. coli tRNA at 42° C. for 2 hours or longer. The $^{32}$P-labeled probe containing a TPA cDNA sequence was added to the prehybridization solution and allowed to hybridize with DNA on filters at 42° C. for 18 hours or longer. The filters were then washed four times in 3XSSC, 0.1% SDS at 65° C. for 30 minutes and once again in 3XSSC at room temperature for 30 minutes. The filters were air-dried and then exposed to Kodak XAR-5 X-ray film with an intensifying screen at −70° C. for 16 hours.

Ten putative positive clones were isolated, subcloned, and re-screened by the method described earlier. Only the clones repeatedly showing positive signals were analyzed by restriction endonuclease cleavage. The clone designated pUPA372 contained the largest cDNA insert, 2.15 kb.

Production of a 5' Sequence of uTPA cDNA

Because even the largest cDNA clone did not contain the entire coding sequence for uTPA, the following strategy was employed to isolate the missing 5' sequence. The mRNA was isolated as described above, except without size selection. First strand cDNA was then synthesized by the primer extension method, as follows. The 72 bp PstI fragment of TPA cDNA (nucleotides 552–624) was annealed to the mRNA in a reaction mixture of 100 ul containing 80% formamide, 10 mM PIPES buffer (pH 6.4), 0.4M NaCl, 0.25 ug of 72 bp fragment, and 70 ug of mRNA. The mixture was heated to 85° C. for 5 minutes and incubated at 50° C. for 20 hours for hybridization. The DNA-RNA hybrid was recovered from the buffer by 3-fold dilution with water and ethanol precipitation at −20° C. overnight. Solubilization and precipitation of mRNA was repeated once more to remove contamination. The conditions for first strand cDNA synthesis were the same as those used in the 3' sequence except the oligo-dT was omitted.

The second strand cDNA was synthesized using a synthetic pentadecamer, CTGTGAAGCAATCAT, as a primer (nucleotides 1–15) for DNA polymerase I-Klenow fragment. Five hundred ng of pentadecamer was annealed to the first strand cDNA in 100 ul containing 50 mM HEPES buffer (pH 6.9), 10 mM MgCl$_2$, and 70 mM KCl at 65° C. for 5 minutes, from 65° C. to 43° C. for 15 minutes, at 43° C. for 15 minutes, and the mixture was then kept on ice before use. Double-stranded cDNA was synthesized and cloned, essentially as described above for the 3' sequence.

After slating, screening and subcloning, a clone, designated pUPA432, was identified, which contained the missing 5' coding sequence and overlaped with clone pUPA372 by 60 bp.

Construction of Full-Length uTPA cDNA

Figure 1C:
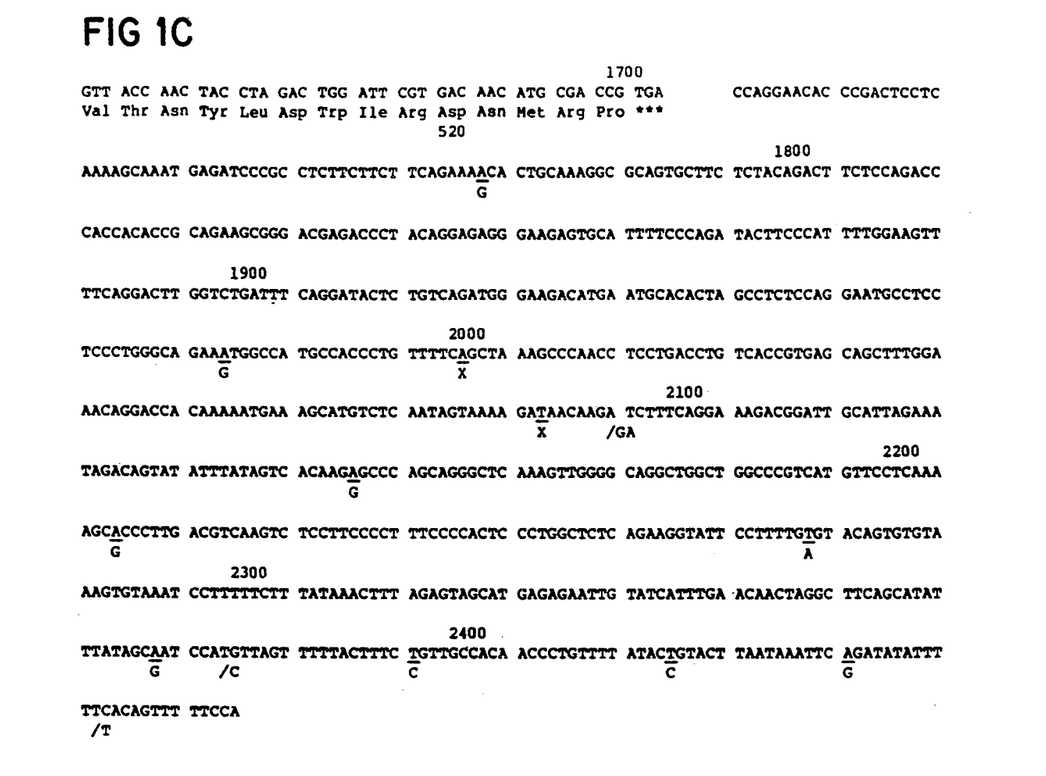

Prior to constructing the entire cDNA clone encoding the human uterine TPA gene, the 5' and 3' portions of the gene were sequenced. This was done by analyzing clone pUPA432 (5' coding sequence) and pUPA372 (3' coding sequence) using a combination of the Maxam-Gilbert chemical degradation method and the Sanger dideoxynucleotide chain termination method. The resulting nucleotide sequence is given in FIG. 1.

Figure 2A:
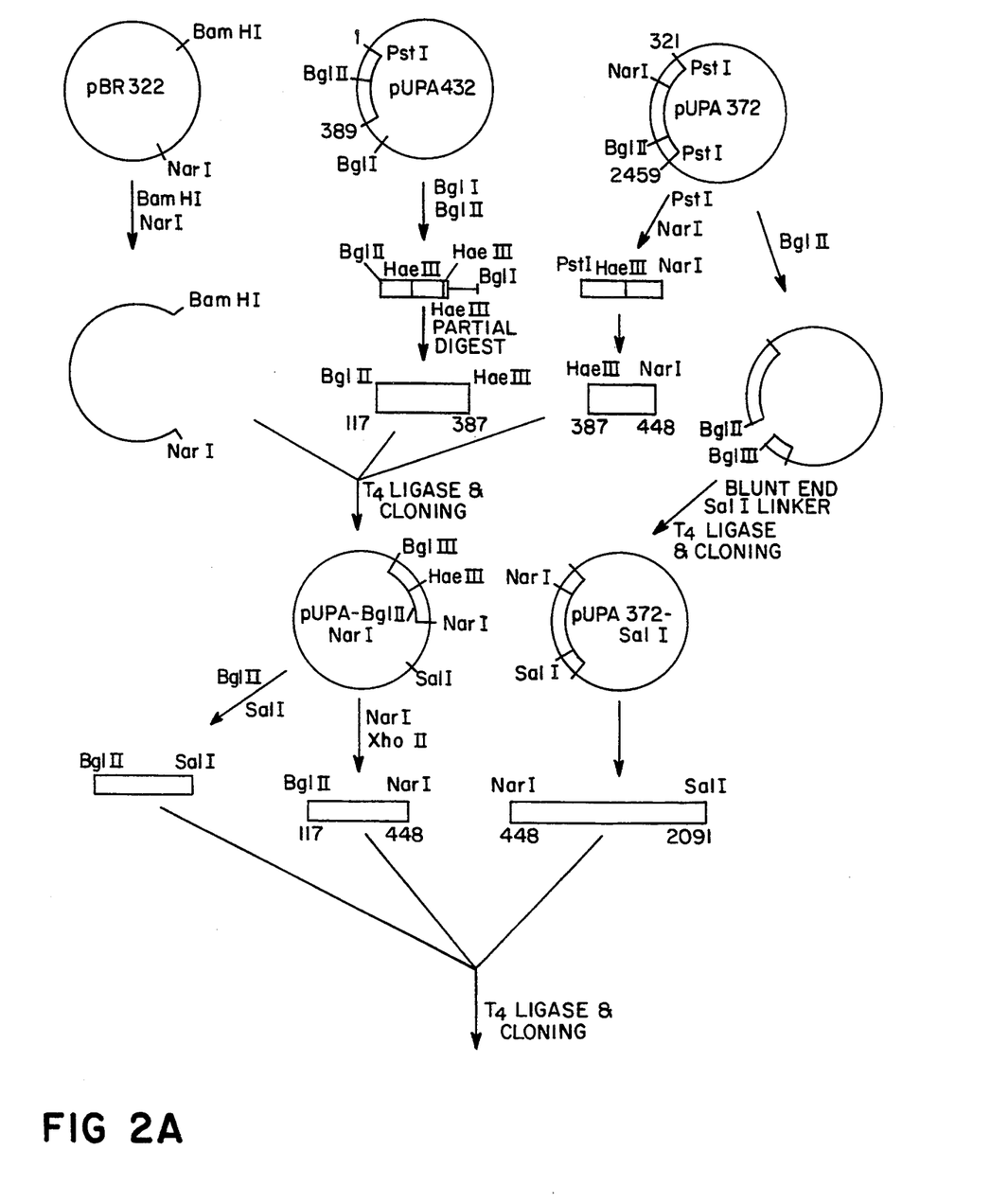
FIG. 2 is a diagrammatic representation of the construction of the complete uTPA cDNA sequence.
Figure 2B:
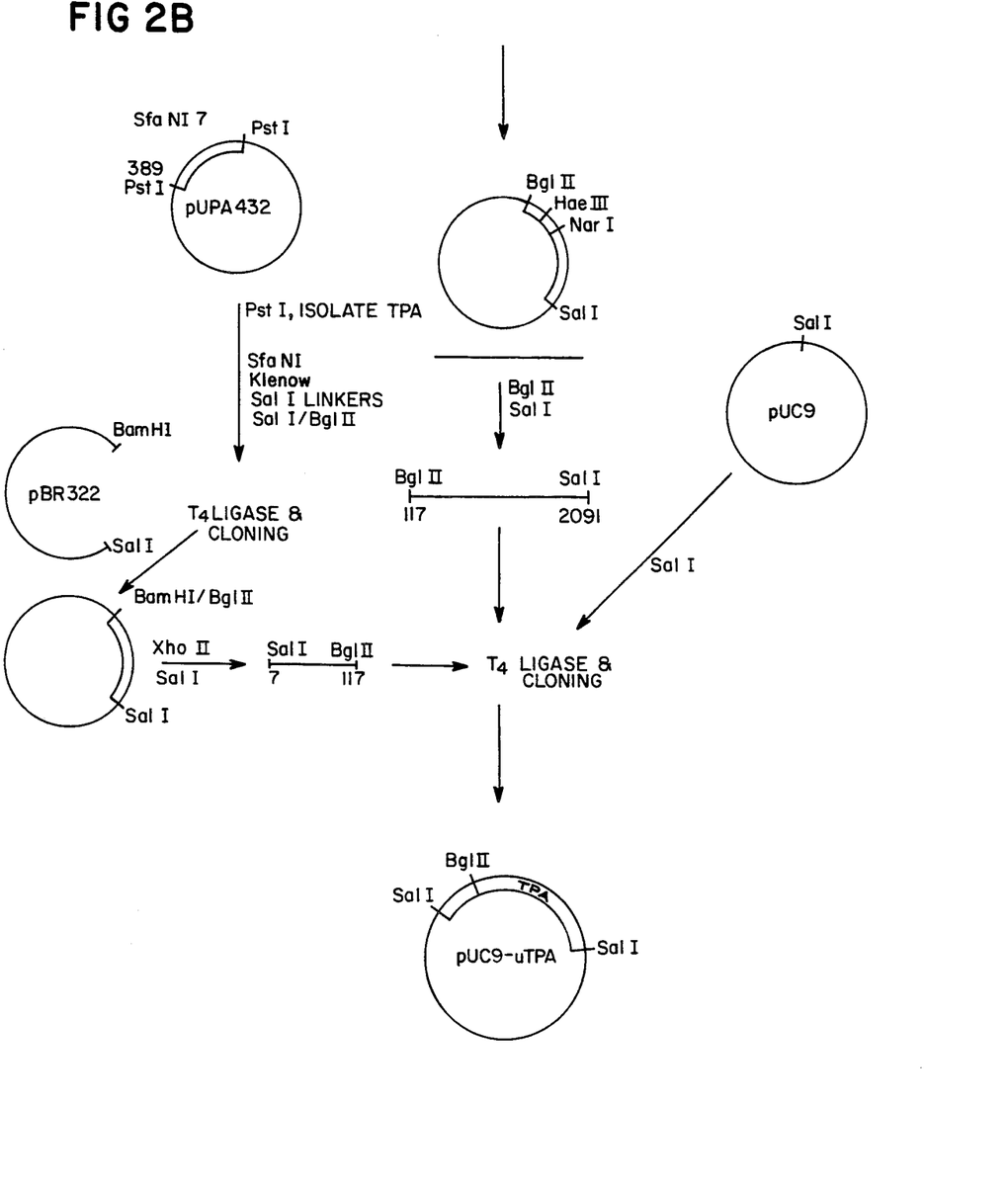

After the sequence of the gene was determined, a complete cDNA gene was constructed, as illustrated in FIG. 2. Plasmid pUPA432 (5' sequence) was first digested with a combination of BglI and BglII. The 400 bp BglI-BglII fragment was isolated from polyacrylamide gel and further digested with HaeIII to partial completion. The resulting Bgl II-Hae III fragment (nucleotides 117–387) was purified by electrophoresis on polyacrylamide gel. Fragment PstI-NarI (nucleotides 321–448) was isolated by a combination of PstI and NarI digestion and subsequent gel electrophoresis. This fragment was further digested with HaeIII to generate the 61 bp HaeIII-NarI fragment. Both BglI-HaeIII and HaeIII-NarI fragments were cloned in pBR322 linearized by a combination of BamHI and NarI digestion. From the resulting clone, designated pUPA-BglII/-NarI, the BglII-NarI fragment (nucleotides 117–448), and the larger BglII-SalI fragments were isolated.

In plasmid pUPA372 the BglII site at nucleotide 2091 was converted into a SalI site by digesting the plasmid with BglII, forming blunt ends with DNA polymerase I, adding SalI linkers, and then generating pUPA372-SalI by cloning in *E. coli*. Subsequent cleavage of pUPA372-SalI by NarI and SalI double digestion produced a NarI-SalI fragment (nucleotides 448–2091).

Next, the leader sequence of uterine TPA cDNA was engineered from pUPA432 by removing the G-C tail and introducing a SalI site. This SalI site was introduced by isolating cDNA from PstI digests, cleaving at the 5' untranslated region with SfaNI, forming blunt-ends with DNA polymerase I, adding a SalI linker, digesting with a combination of SalI and BglII, and cloning in a pBR322 vector linearized with BamHI and SalI double digestion. The engineered uterine TPA leader was excised from the vector by a combination of XhoII and SalI digestion. This SalI-BglII fragment (nucleotides 7–117 was spliced to the SalI-BglII fragment (nucleotides 117 –2091) formed by ligating the BglII-NarI, NarI-SalI, and BglII-SalI fragments described above.

After ligation and transformation, the full-length uterine TPA gene flanked by SalI sites was cloned in a pUC9 vector. This pUC9-uTPA plasmid was used as an intermediate for further construction of expression vectors.

YEAST EXPRESSION VECTORS

Yeast expression vectors can be made in which a yeast promoter and signal sequence precede the portion of the uTPA cDNA encoding the mature protein (and excluding the uTPA signal), or, alternatively, the vector can include a yeast promoter, but no yeast signal, in which case the uTPA cDNA encodes the immature protein, including the TPA signal. In other words, the signal sequence can either be of yeast or uTPA origin. Except for the fact that the particular vectors described below express active uTPA, rather than other proteins, they were made according to methods similar to those described in Lemontt et al. U.S. Pat. Appln. Ser. Nos. 636,365 and 629,202, hereby incorporated by reference. Only the structures of the vectors, and not the details of their construction, will therefore be given.

Vector Containing Yeast Signal

Figure 3:
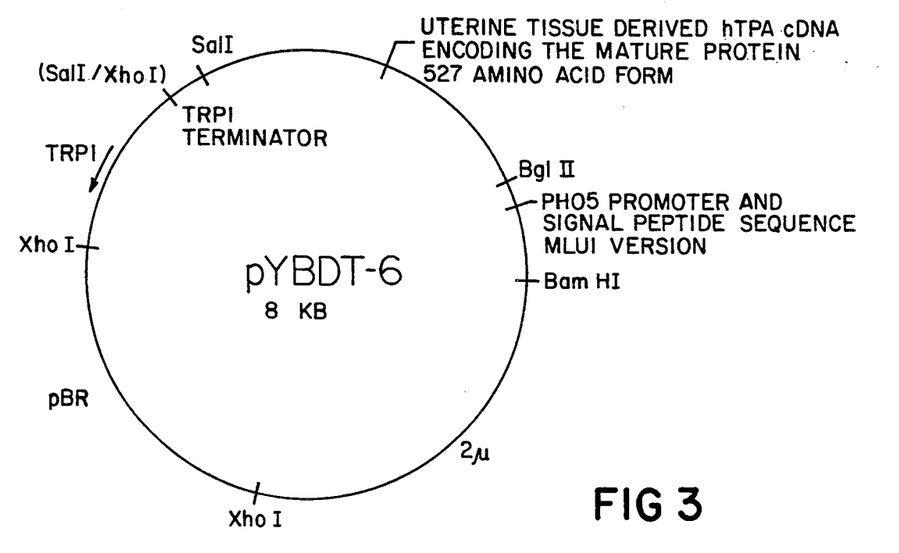
FIG. 3 is a diagrammatic representation of a yeast (Saccharomyces cerevisiae) expression vector of the invention.

Referring to FIG. 3, yeast expression vector pYBDT-6 is composed of the following DNA fragments (beginning at the unique BamHI site and moving counter-clockwise):

BamHI-BglII, containing the yeast PHO5 promoter and signal sequences, plus 9 base pairs of synthetic DNA sequence encoding Cly(-6), Ala (-5), Arg (-4) as shown in FIG. 1. this fragment is about 0.6 kb long.

BglII-SalI, containing uterine-derived TPA cDNA, described above; this fragment encodes the mature protein and also contains about 0.4 kb of 3' untranslated region; this fragment is about 1,975 kb long.

SalI-(SalI/XhoI), containing a TRP1 "terminator" region which originally was the HindIII-BglII fragment of the TRP1 gene; this fragment is about 0,240 kb long.

(SalI/XhoI)-XhoI, containing the EcoRI-SglII fragment of the TRP1 gene.

XhoI-XhoI; this is a fragment of pBR322 containing AMP$^R$ and ORI: this approximately 2.1 kb fragment roughly corresponds to the region of pBR322 from position 2246 to position 4361 on the pBR322 map.

XhoI-BamHI; this fragment is the approximately 2.2 Kb EcoRI fragment of the 2-micron circle, "B" form.

Vector Containing TPA Signal

Figure 4:
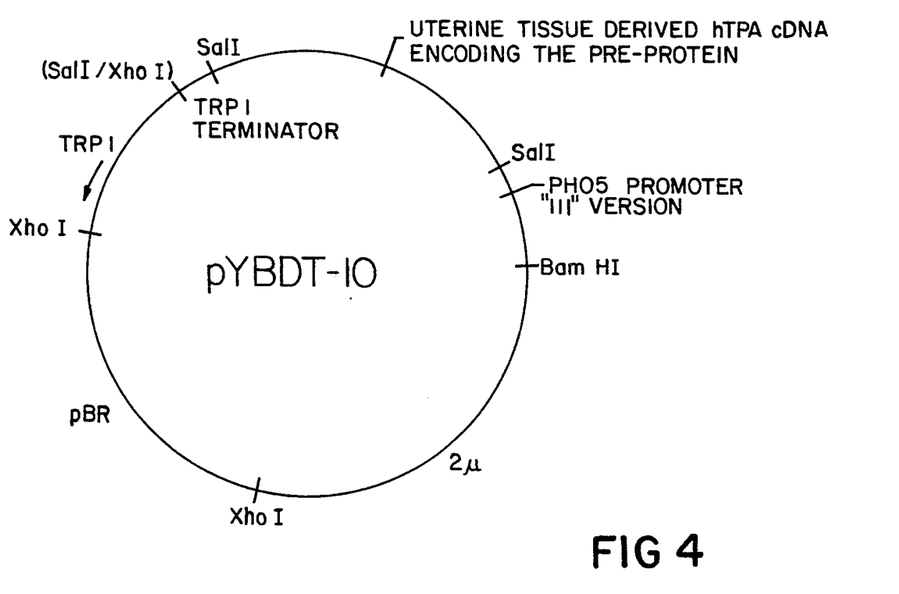
FIG. 4 is a diagrammatic representation of another yeast expression vector of the invention.

Referring to FIG. 4, yeast expression vector pYBDT-10 is identical to pYBDT-6, except for two fragments:

1) rather than the BamHI-BglII fragment, pYBDT-10 has BamHI-SAiI, which contains a PHO5 promoter region in which the 3' insertion site has been SalI linkered; this fragment is about 0.52 kb long.

2) rather than the BglII-SalI fragment, pYBDT-10 has SalI-SalI, which contains uterine TPA cDNA encoding the immature protein, including the signal.

MAMMALIAN CELL EXPRESSION VECTORS

In addition to yeast expression vectors, mammalian expression vectors can be made for the production of human uterine TPA. As in the case of yeast, a variety of auxiliary DNA fragments can be used to effect transcription and translation of the uterine TPA DNA, as well as effect host cell transformation.

There will now be described particular expression vectors for the production of human uterine TPA in cultured mammalian cells. The described vectors are maintained in *E. coli* strain RF322 prior to their use in the transformation of host mammalian cells.

Plasmid CL28-uTPA-BPV

Figure 5:
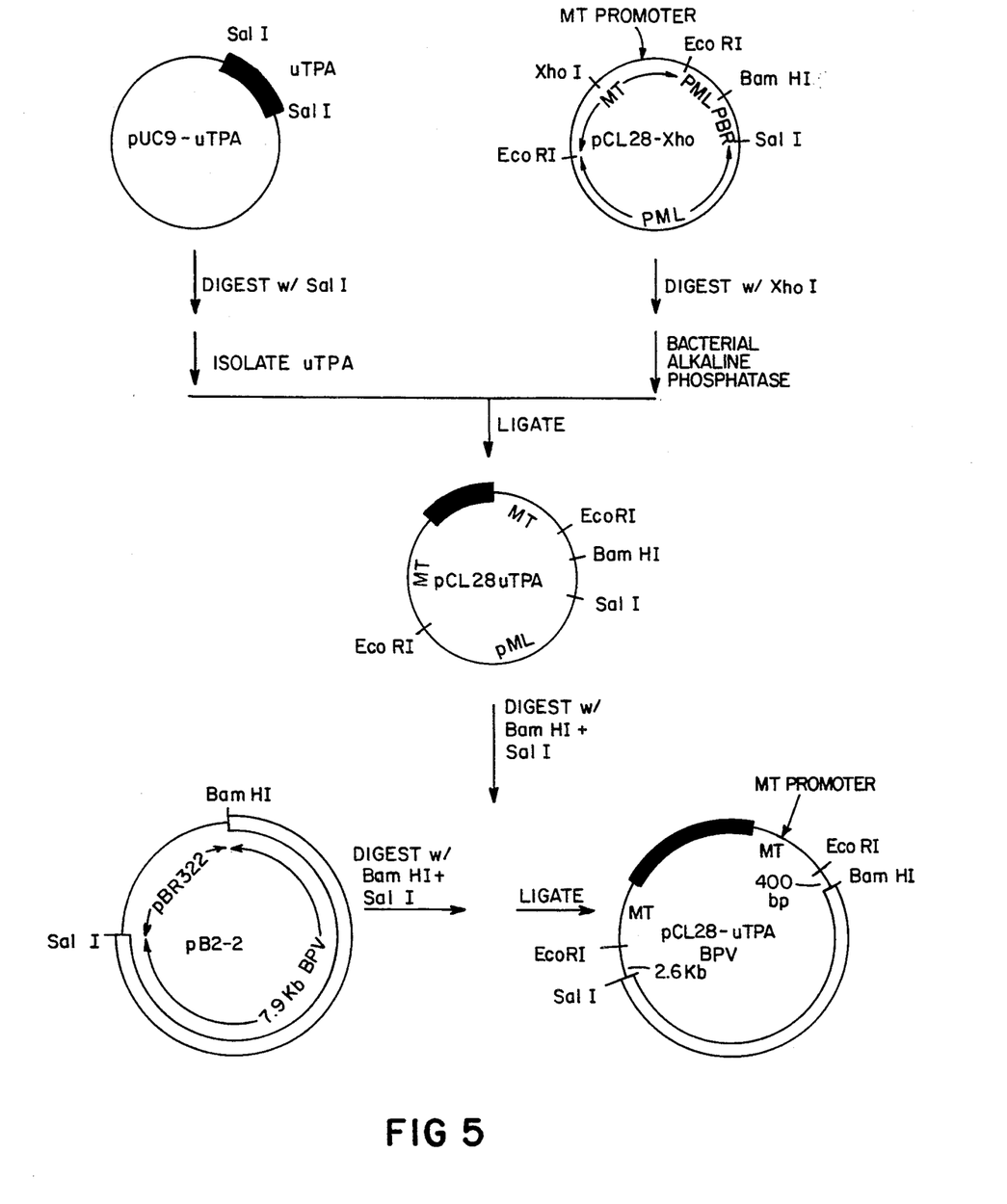
FIG. 5 is a diagrammatic representation of the construction of a mammalian expression vector of the invention.

Referring to FIG. 5, the mammalian expression vector CL28-uTPA-BPV, in which the uTPA gene is under the control of the mouse metallothionein (MT) promoter and transformation of host cells is effected by bovine papilloma virus (BPV), is constructed as follows.

The two starting plasmids are pUC9-uTPA (containing the TPA gene; described above), and pCL28-Xho, a derivative of pCL28 (described, as pJYmmT(E), in Hamer et al. (1983) J. Mol. Applied Gen. 1, 273) in which SV40 DNA has been removed and in which an XhoI restriction site rather than a BglII site is positioned near the MT promoter.

Plasmid pUC9-uTPA was digested with SalI and the 2098 bp fragment containing the uTPA gene was inserted in the XhoI site of pCL28-Xho to form pCL28-uTPA, in which the uTPA gene is between the MT promoter and MT structural gene.

In the next step, plasmid pB2-2, containing the entire BPV genome, was digested with BamHI and SalI to yield a fragment containing the entire BPV genome and a region of pBR322 DNA. This fragment was inserted into pCL28-uTPA which had been linearized by digestion with BamHI and SalI, to yield plasmid pCL28-uTPA-BPV.

Plasmid pBMTH-uTPA

Figure 6:
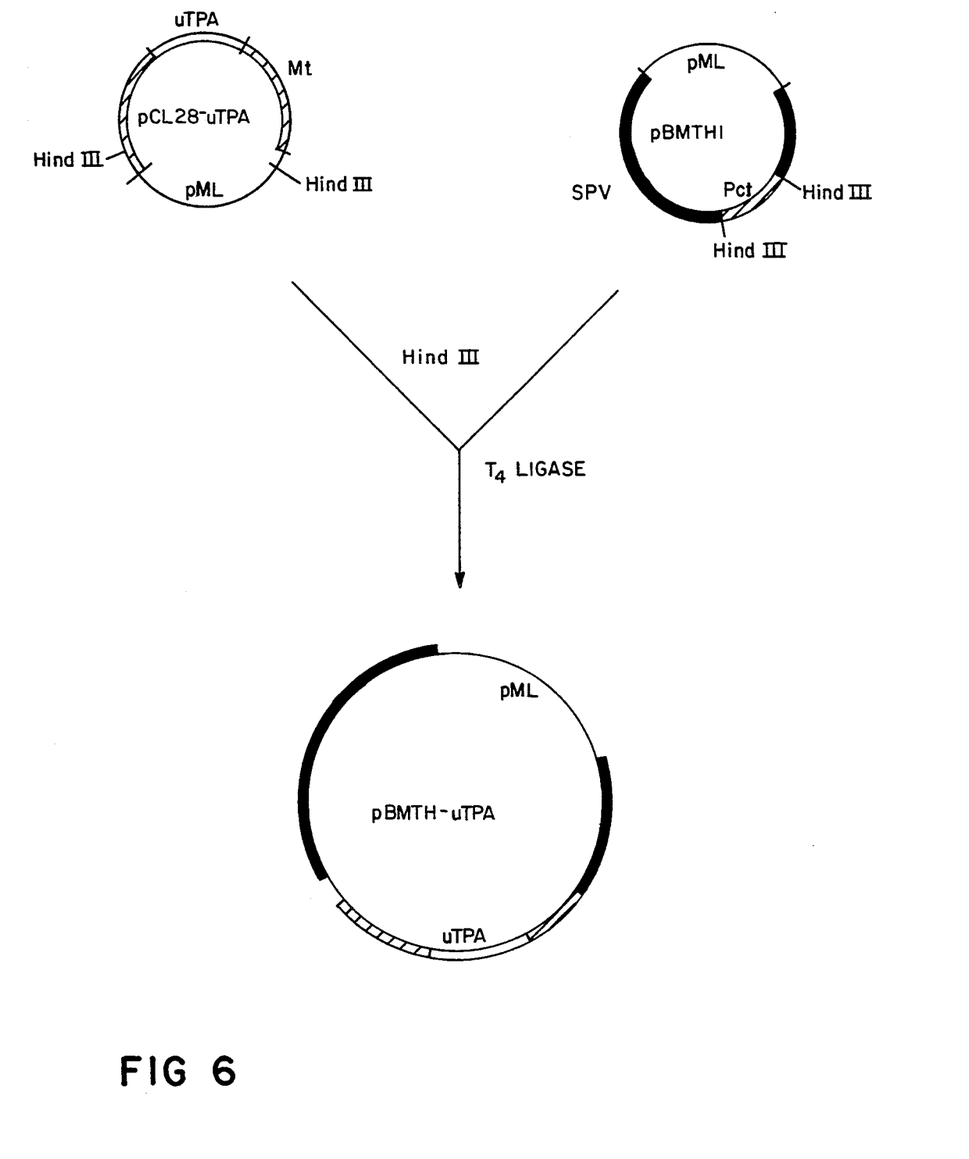
FIG. 6 is a diagrammatic representation of another mammalian expression vector of the invention.

Referring to FIG. 6, mammalian expression vector BMTH-uTPA was constructed using CL28-uTPA, described above, and pBMTH1, obtained from Dean Hamer of the National Institutes of Health, Bethesda, Md. Plasmid pBMTH1 contains the MT structural gene, and the MT promoter flanked on one side by the 69% transforming region of BPV and on the other side by the remaining 31% of BPV.

The HindIII fragment of pBMTH1, containing the MT gene, was removed and replaced by the HindIII fragment from pCL28-uTPA containing the uTPA gene inserted into the MT gene, to yield plasmid pBMTH-uTPA.

Plasmid pCAT

Figure 7:
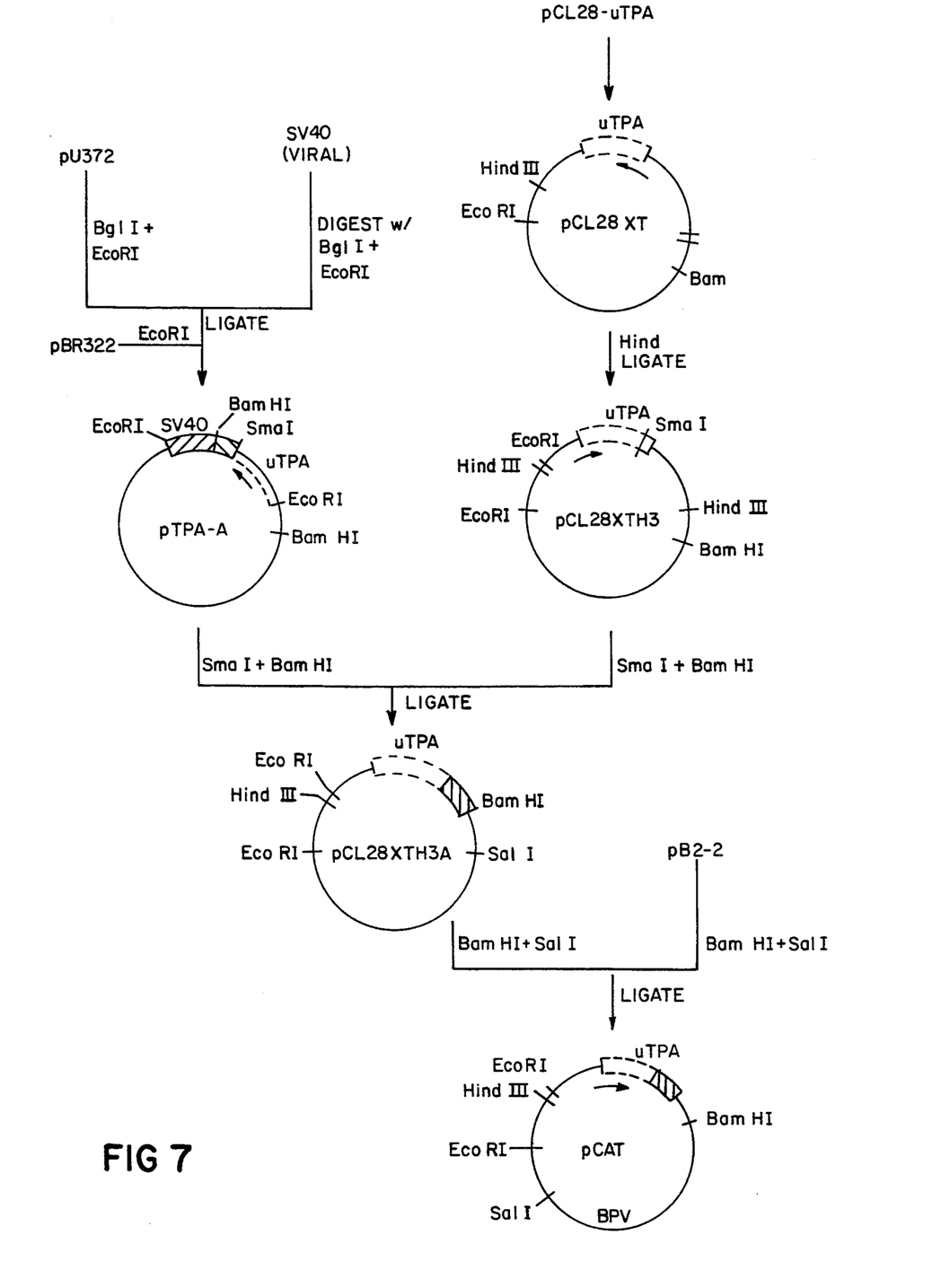
FIG. 7 is a diagrammatic representation of another mammalian expression vector of the invention.

Referring to FIG. 7, plasmid pUPA372 (uterine TPA cDNA plasmid containing uTPA sequences starting from 372 bp, and the remainder of the sequence, as shown in FIG. 1) was cut with BglII and EcoRI and ligated to viral SV40 DNA cut with BclI and EcoRI. The ligation mixture was cloned into the pBR322 EcoRI site to obtain the plasmid pTPA-A.

In order to change the orientation of uTPA transcription, the plasmid pCL28-uTPA (FIG. 5) was cut with HindIII and religated at high DNA concentration. After screening by cutting with EcoRI and BamHI, the recombinant plasmid pCL28XTH3 was selected.

pTPA-A and pCL28XTH3 were both digested with SmaI and BamHI and ligated to obtain CL28XTH3A, which contains a 237-bp SV40 DNA fragment replacing a 1.5 kb metallothionein fragment in pCL28XTH3. In this construction, uTPA expression depends on the use of the MT promoter and, downstream from the uTPA gene (the MT structural gene being deleted), SV40 early poly A signal sequences alone.

Plasmids pCL28XTH3A and pB2-2 (described above) were cut with BamHI and SalI and BPV DNA from pB2-2 was inserted as a BamHI-SalI fragment. The resulting construct is pCAT.

TRANSFORMATION OF MAMMALIAN CELLS pCL28-uTPA-BPV or pBMTH-uTPA plasmid DNA was introduced into mouse C127 cells using a modification of the transfection technique of Wiglet et al. (1977) Cell 11, 223, as follows.

5 ug of DNA were added to 0.5 ml of a 240 mM $CaCl_2$ solution containing 10 ug of carrier salmon sperm DNA. This solution was bubbled into an equal volume of 2xHBS (280 mM NaCl, 20 mM Hepes, and 1.5 mM sodium phosphate) having a pH of 7.1. The calcium phosphate was allowed to form for 30 minutes at room temperature, and $5 \times 10^5$ C127 cells were plated 24 hrs prior to transfection. While the calcium phosphate precipitate was forming, the cell growth medium was changed. The calcium phosphate precipitate was added to the cells and incubated for 6–8 hr. at 37 C. The DNA was removed and the cells were exposed to 20% glycerol in phosphate buffered saline (PBS), pH 7, for 1–2 minutes at room temperature. The cells were washed with PBS, and 10 ml of Dulbecco's modified medium with 10% fetal calf serum (MA Biologicals), penicillin/streptomycin and 10 mM glutamine (GIBCO) was added. The medium was changed 24 hrs later and every 3–4 days thereafter. Foci could be detected after 14–21 days and isolated by the cloning ring method after 21 days. The foci were expanded for analysis.

Transformed cells were cultured using conventional techniques, and uTPA harvested continously from the culture medium, using conventional techniques.

Transformed mouse C127 cells containing pCL28-uTPA-BPV or pBMTH-uTPA can exist for up to 60 days in confluent cell culture if the media is changed every 24–28 hrs. The cells continually double, in the flask or roller bottle, with growth characteristics of transformed cells. Transformed C127 cells containing pCAT exist in cell culture for shorter periods but produce uTPA at a higher rate.

The combination of a strong metallothionein promoter controlling uTPA production in the BPV vector (which allows amplified DNA copy number) and the continuous growth properties of the BPV transformed cells provide an optimal system for scale up production of the uTPA.

TRANSFORMATION OF YEAST CELLS

Host yeast cells (*Saccharomyces cerevisiae*) were transformed using the yeast expression vectors according to standard techniques, generally as described in Beggs (1978) Nature 275, 104–109. Host cells carry a trpl mutation which causes tryptophan auxotrophy, while the plasmids carry a functional TRP1 gene. Transformants are thus selected as tryptophan prototrophs. Transformed host yeast cells were cultured in a standard yeast culture medium generally using the method described in Botstein and Davis, "Principles and Practice of Recombinant DNA Research with Yeast" in The Molecular Biology of the Yeast Saccharomyces: Metabolism and Gene Expression, pp 607–636, Cold Spring Harbor Laboratory, Cold Spring Harbor, N.Y. 1982.

Rather than using circular plasmid pYBDT-6 and pYBDT-10 to transform host yeast cells, these vectors can be linearized prior to transformation using XhoI, which removes the pBR322 sequence, and the linearized vector used for transformation; recircularization occurs within the host yeast cell. This procedure has the potential advantage of removing all bacterial sequences, which carry the potential for reducing vector copy number or otherwise interfering with uTPA expression.

Extraction and Purification of uTPA from Culture Media

Active uterine TPA produced by yeast is recovered from extracts prepared by mechanically disrupting the cells using glass beads. Active uterine TPA produced by recombinant mammalian cells is recovered from the host cell culture medium. Purification of active uTPA from cell extracts or culture media generally involves the steps of 1) liquid/liquid phase extraction or an initial filtration step; 2) hydrophobic affinity chromatography; 3) antibody affinity chromatography; and 4) gel filtration chromatography. In more detail, these steps are carried out as follows.

Liquid/Liquid Phase Extraction

The first step cam be liquid/liquid phase extraction or, more preferably, an initial filtration step. In general, liquid/liquid extraction is carried out by combining the culture medium with the water-soluble, polymeric compounds, e.g., Dextran and polyethylene glycol, which cause the formation of two layers, one of which is discarded. (Liquid/liquid phase extraction is a well-known protein extraction technique described, e.g., in Johansson et al. (1973) Eur. J. Biochem. 33, 379–386.)

The preferred liquid/liquid extraction step involves diluting serum-free or serum-containing medium containing uTPA to 0.1%, v/v, with Tween 80 and then adding powdered Dextran to a final concentration of 4% (40 g/liter).

The Dextran is mixed until in solution and then polyethylene glycol (PEG) 6000 is added to a final concentration of 12% (120g/liter). The solution is mixed well and then centrifuged in 200 ml bottles at 1200 RPM on an International refrigerated centrifuge for 10 min to effect phase separation. The upper phase is decanted and the lower Dextran phase pooled. Recovery of 75% of the initial uTPA activity with approximately 40% of the initial protein is achieved. A 6-fold concentration with a volume reduction of over 50% is achieved. The liquid/liquid extraction procedure is found to be effective despite the presence of cellular debris, and complex growth factors, e.g. Epidermal Growth Factor, transferrin, and insulin, commonly found in serum-containing growth media.

It has been found that, although the above-described liquid/liquid extraction step can be used, the conditioned media can be initially clarified, for the next hydrophobic affinity chromatography step, in a simpler manner by passing the conditioned media through a three-micron profile filter. The resulting clarified media is then subjected, without a concentration step, to hydrophobic affinity chromatography, as follows.

Hydrophobic Affinity Chromatography

This step involves bonding the uTPA in the material from the previous step to a dye, e.g., Trisacryl Blue (LKB), Macrosorb Blue, or CM Affi-Gel blue (BioRad), capable of binding uTPA but not some of the other proteins in the culture medium. (Affi-Gel blue has been used in a different purification scheme for a plasminogen activator isolated from a human neuroblastoma line, in conjunction with $(NH_4)_2 SO_4$ precipitation and p-aminobenzamidine-Sepharose chromatography; Biochim. Biophys. Acta (1980) 704, 450–460.)

This step is preferably carried out as follows. If liquid/liquid extraction was carried out in the first step, the volume of the Dextran phase from the previous step is doubled by addition of $H_2O$ to reduce viscosity. Otherwise, the filtered, clarified media is used without dilution or concentration. Fifty ml of Trisacryl blue (LKB) matrix equilibrated with phosphate buffered saline, 0.1% Tween, pH 7.2, are added per liter. The solution is mixed gently at 4° C. for 2 hours and then washed in batch with phosphate buffered saline, 0.1% Tween, pH 7.2, and 0.5M NaCl, 0.02M Phosphate, 0.01% Tween, pH 7.2. The TPA-containing material is then poured into a gel filtration column at a load factor of 50%, and run at a linear velocity of 85 cm/hr. The material is eluted from the Trisacryl blue matrix with 3.0M KSCN, 0.02M Phosphate, 0.01% Tween, pH 7.2.

A four-fold concentration from the previous steps is achieved by this step. This binding of the uTPA directly from the Dextran phase also permits a rapid change in salt concentration and increases uTPA purity.

Rather than using 3M KSCN for the above elution step, other salts, e.g. NaCl, can be used. A 0.15 to 3.0 M NaCl gradient, for example, provides a greater degree of purification, but at a cost of concentration.

As is mentioned above, other matrixes, in additon to Trisacryl blue, can be used in this step. One example is CM Affi-Gel blue (Bio Rad), which binds uTPA equally well and elutes uTPA in the same pattern as Trisacryl blue.

Concentrations of reagents can be varied at each stage of the above two purification steps. For example, the Dextran and PEG concentrations used in the liquid/liquid extraction step can be changed so as to shift the uTPA activity into the PEG (upper) phase, rather than the Dextran (lower) phase; in this case, the decanted material would be saved and the lower phase discarded.

Affinity Chromatography

The next step, in which the bulk of the purification is achieved, involves affinity chromatography using anti-TPA antibodies immobilized on a solid support column. Either polyclonal or monoclonal anti-TPA antibodies, made according to conventional techniques, can be used.

The preferred affinity chromatograhy step is carried out as follows. The material eluted from the Trisacryl matrix is dialyzed against 1.0M NaCl, 0.01% Tween, 0.02M phosphate, pH 7.4, to remove the KSCN. The material is then sterile filtered through a 0.22 micron filter. The eluant is then passed very slowly, at 4° C., over a monoclonal anti-TPA antibody Sepharose matrix (The ant body was obtained from Dr. Keld Dano, University Copenhagen Inst. PathiAnatomy) capable of binding all of the uTPA activity contained in the eluant. (Anti-TPA monoclonal antibodies are commercially available from Bioscott, Ltd, Scotland, or American Diagnostica.) The antibody is coupled to CNBr-activated Sepharose, at 5 mg antibody/ml resin, on a 100 ml column. The antibody matrix is pre-equilibrated in 0.1M Tris, 0.1% Triton X-100, pH 8.0, washed with 1.0M NaCl, 0.1% Triton X-100, 0.05M Tris, pH 8.0, and eluted with 3.0M $NH_4SCN$, 0.1% Triton X-100, 0.05M Tris, pH 8.0. (The Triton X-100 in the final step can be replaced by Tween 80 with similar results.) Elution is carried out at a linear velocity of 12 cm/hr, giving greater than 90% recovery. One-ml fractions are collected and the majority of the uTPA activity is eluted in the first 3 to 4 column volumes.

The uTPA-containing material can be applied to the antibody/Sepharose matrix in salt as concentrated as 1.5M NaCl without affecting binding efficiency. uTPA can be eluted by lowering the pH to about 2.5 with, e.g. 0.1 M glycine, rather than by using 3M $NH_2SCN$, but $NH_2SCN$ is preferred because it allows recovery of uTPA in a smaller volume, since no neutralization is necessary. $NH_2SCN$ also keeps the protein in a more stabilizing environment.

Following the antibody affinity step, a hydrophobic or sizing HPLC step can be carried out to increase purity to greater than 97%.

Gel Filtration Chromatography

This step removes some minor high molecular weight contaminants present in the eluate from the immunoaffinity column. The gel affinity column is packed with Toyopearl TSK and run in 0.01 M phosphate-1.6 M $NH_4$ SCN and monitored for $A_{280}$ and for activity. Fractions across the peaks are further analyzed by gel electrophoresis, followed by silver staining. Western blots are performed on selected pools.

Purification Monitoring

Purification is monitored throughout the above procedure as follows. Samples of fractions at each stage are diluted with 0.5M NaCl, 0.01% Tween, 0.02M phosphate, pH 7.4, and amidolytic activity assayed with S2251 chromogenic substrate coupled with human plasminogen activator in the presence of fibrinogen (described in Campbell et al. (1982) Clin. Chem. 28, 1125–1128). Absorbance at 280 nm of samples diluted with $dH_2O$ is recorded. Purification is also monitored by nonreducing and reducing SDS polyacrylamide gel electrophoresis.

The purified uTPA recovered from the antibody/Sepharose column exhibits less than 3% contamination on SDS PAGE electrophoresis. Under reducing conditions, some 2-chain TPA (the activated form; single chain is the preferred form) is observed. The 2-chain form can be prevented by adding Aprotinin to the buffers used in the purification steps.

CHARACTERIZATION OF UTERINE TPA AND UTERINE TPA cDNA

As mentioned above, there is shown in FIG. 1 the nucleotide sequence of uterine TPA cDNA, along with the deduced amino acid sequence of the uterine TPA encoded by the cDNA. The tentative preprosequence corresponds to amino acids −38 to −1. The vertical lines in FIG. 1 preceding amino acids +1, −3, and −6 indicate cleavage sites. Potential glycosylation sites are indicated by "CHO" at the Asn residues. The plasmin cleavage site (at which single-chain uTPA is converted to 2-chain uTPA) is indicated by the arrow. The conserved sequence of serine proteases at the active center is underlined.

FIG. 1 shows the difference in nucleotide sequence between uterine TPA cDNA and the Bowes melanoma cDNA described in Goeddel et al. European Pat. Appln. 0 093 619, mentioned above. Positions at which the Bowes DNA is missing a nucleotide present in uterine cDNA are marked with "X." Positions at which uterine cDNA is missing nucleotides present in Bowes cDNA are indicated by a "/", followed by the missing nucleotides.

PARTIALLY-AND NON-GLYCOSYLATED TPA'S

As described in the Summary of the Invention, above, the present invention provides, in addition to recombinant DNA-produced human uterine TPA, expression vector-encoded TPA's which are less than fully glycosylated when produced in mammalian host cells.

Figure 8:
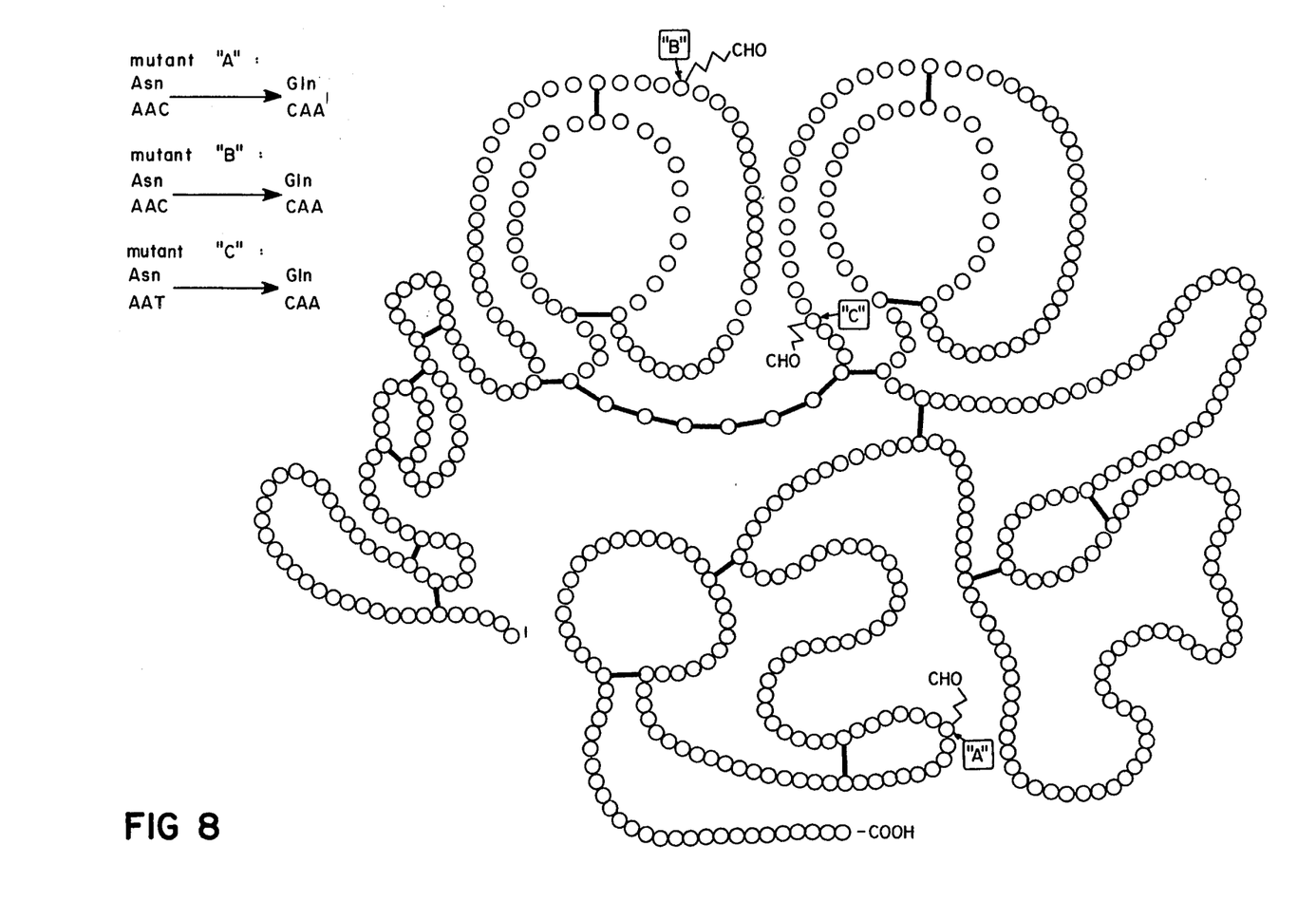
FIG. 8 is a diagrammatic representation of the base sequence of the human uterine TPA gene, showing points of N-glycosylation.

Referring to FIG. 1, naturally occurring human TPA is N-glycosylated at three asparagine residues on the molecule (positions 114, 181, and 445). The signal for N-linked glycosylation is Asn-X-(Ser or Thr). The strategy we employed to prevent glycosylation at one or more of these sites involved substitution at those sites in the TPA-encoding DNA molecule of a CAA codon (encoding glutamine) for AAC or AAT (encoding asparagine). As will be described in more detail below, these mutant sites (A, B, and C in FIG. 8) were constructed by in vitro mutagenesis using the mismatched primers TCGGTGACTGTTCCTTTGAAG-TAAATGTTGT, CAACGCGCTGCTTTG-CCAGTTGGTGCA, and GTAGGCT-GACCCTTGGCCCAAAGTAGCA, respectively.

Using mutant A single stranded DNA as a template, we have also contructed mutants A+B, A+C, and A+B+C. Finally, recombining mutants B and C yielded mutant B+C. Thus we have constructed all seven possible combinations of non- or partially-glycosylated human TPA mutants.

Site-Specific Mutogenesis

In vitro site-specific mutagenesis was carried out using a modification of the method first described in Smith et al. (1979) Gene 8, 81–87, 99–106, as follows.

The mismatched oligonucleotide primers described above were synthesized on an Applied Biosystems automated synthesizer, using conventional techniques.

DNA encoding human uterine TPA (described above) was cloned into phage M13 mp18 (available from Pharmacia or New England Biolabs). The single-stranded phage DNA containing the sense strand of TPA was used as a template for oligonucleotide-directed mutagenesis. Each mismatched oligonucleotide primer was annealed to the template at 65° C. for ten minutes and then at room temperature for ten minutes in a reaction mixture containing 20 mM Tris-HCl, pH 7.5, 10 mM $MgCl_2$, 50 mM NaCl, 1 mM dithiothreitol, 0.2 pmoles of single-stranded mp18-TPA DNA, and 20 pmoles of 5' phosphorylated mismatched oligonucleotide. An equal volume of buffer PE containing 30mM Tris-HCl, pH7.5, 10 mM $MgCl_2$, 2 mM mercaptoethanol, 1 mM each of dATP, dCTP, dGTP, dTTP, and 1 mM of ATP were then added to the annealing reaction mixture. Primer extension was carried out by the addition of 5–10 units of DNA polymerase-Klenow fragment and 3–5 units of T4 ligase and incubation at 16° C. overnight.

The reaction mixture was diluted and used to transform competent JM105 cells. The phage plaques were screened by in situ mutagenic oligonucleotide plaque hybridization, using [12]P-labeled mismatched primer to screen for the desired mutants; this method is based on the desired mutant being perfectly matched with the primer, while wild-type DNA contains one or more mismatches. Thus, under appropriate hybridization conditions, the degree to which the mismatched primer hybridizes to the mutant is greater than that to wild-type, and this difference allows the selection of desired mutants.

Putative mutants were isolated and characterized by restriction endonuclease digestion and by DNA sequencing. The desired mutants were then cloned and expressed in the pCL28-BPV system described above for normal uterine TPA, by excising the replicative form of the appropriate M13 mp18-TPA mutants, inserting this DNA into the pCL28-BPV expression vector, and transforming C127 mouse cells with vector DNA. Transformants were isolated and screened for the production of TPA using an ELISA assay. Most TPA produced is secreted into the culture medium, facilitating purification.

The effect which partial or non-glucosylation has on the half-life of the TPA's was determined by measuring half-lives of TPA's and comparing them and to the known half-life of fully glycosylated TPA. Half-lives were measured in rabbits by drawing blood samples at different times after injection and measuring the activity and amount of TPA present using the fibrin plate test and an ELISA assay, respectively. The in vivo clearance via the liver, of fully glycosylated TPA from circulate blood is very rapid, with a biological half-life of about two minutes (Thromb. Haemostas. 46, 658, 1981). Thus TPA is normally administered not by injection, but by infusion of a large amount over a three-hour period. A longer half-life may permit treatment by injection rather than infusion, because smaller amounts will be needed to achieve clot lysis.

DEPOSITS

The following have been deposited with the Agricultural Research Culture Collection (NRRL), Peoria, Ill. or the American Type Culture Collection (ATCC), Rockville, Md:

pYBDT-6, maintained in *E. coli,* NRRL Accession No. B-15883;

pYBDT-10, maintained in *E. coli,* NRRL Accession No. B-15884;

mouse C127 cells transformed with pCAT, ATCC Accession No. CRL8625.

Applicants' assignee, Integrated Genetics, Inc., acknowledges its responsibility to replace these cultures should they die before the end of the term of a patent issued hereon, and its responsibility to notify the NRRL and ATCC of the issuance of such a patent, at which time the deposits will be made available to the public for at least 30 years after the date of deposit. Until that time the deposits will be made available to the Commissioner of Patents under the term of 37 CFR §1.14 and 35 USC §112.

Use

The uTPA of the invention will be admixed with a pharmaceutically acceptable carrier substance, e.g., saline, and administered orally, intravenously, or by injection into affected arteries or the heart. Administration will be generally as is carried out for two currently used blood clot lysing enzymes, streptokinase and urokinase.

Other embodiments are within the following claims.

We claim:

1. A recombinant DNA molecule which encodes human tissue plasminogen activator (TPA) and which differs from a naturally occurring DNA molecule encoding naturally occurring human TPA in that, in place of at least one of the Asn codons in the three DNA sequences which encode an Asn-X-(Ser or Thr) signal for N-linked glycosylation in said naturally occurring human TPA corresponding to amino acids 114–116, 181-184, and 445–447 of FIG. 1A–C hereof, there is substituted a Gln codon.

2. A mammalian cell transformed with the recombinant DNA molecule of claim 1.

3. The recombinant DNA molecule of claim 1 wherein one said substituted Gln codon replaces a naturally occurring Asn codon encoding an amino acid in the glycosylation signal corresponding to amino acids 114–116 of FIG. 1A–C hereof.

4. The recombinant DNA molecule of claim 1 or claim 3 wherein one said substituted Gln codon replaces a naturally occurring Asn codon encoding an amino acid in the glycosylation signal corresponding to amino acids 181-184 of FIG. 1A–C hereof.

5. The recombinant DNA molecule of claim 4 wherein one said substituted Gln codon replaces a naturally occurring Asn codon encoding an amino acid in the glycosylation signal corresponding to amino acids 445–447 of FIG. 1A–C hereof.

6. The recombinant DNA molecule of claim 1 or claim 3 wherein one said substituted Gln codon replaces a naturally occurring Asn codon encoding an amino acid in the glycosylation signal corresponding to amino acids 445–447 of FIG. 1A–C hereof.

7. The recombinant DNA molecule of claim 1 wherein there is substituted a Gln codon for the naturally occurring Asn codon in two of said three DNA sequences.

8. A method of making active human TPA which lacks one or more of the N-linked carbohydrate moieties of naturally occurring human TPA, said method comprising transforming a mammalian cell with the recombinant DNA molecule of claim 1, culturing said mammalian cell in culture medium under conditions in which said recombinant DNA molecule is expressed to yield said TPA, and isolating said TPA from said cell or said culture medium.

9. The recombinant DNA molecule of claim 1 wherein there is substituted a Gln codon for the naturally occurring Asn codon in one or two of said three DNA sequences.

10. The recombinant DNA molecule of claim 1 wherein there is substituted a Gln codon for the naturally occurring Asn codon in one of said three DNA sequences.

11. The recombinant DNA molecule of claim 1 wherein there is substituted a Gln codon for the naturally occurring Asn codon in three of said three DNA sequences.

12. Modified tissue plasminogen activators wherein the modification consists of amino acid substitutions for at least one residue in one, or more than one, of the three Asn-X-(Ser/Thr) glycosylation signals corresponding to amino acids 114–116 181-184, and 445–447 of FIG. 1A–C hereof.

13. Modified human tissue plasminogen activator (TPA) which differs from naturally occurring human TPA in that, in at least one of the three Asn-X-(Ser or Thr) signals for N-linked glycosylation in said naturally occurring human TPA corresponding to amino acids 114–116, 181-184, and 445–447 of FIG. 1A–C hereof, there is substituted a Gln for the Asn.

14. The modified human TPA of claim 13 wherein there is substituted a Gln for the Asn in one or two of said three glycosylation signals.

15. The modified human TPA of claim 13 wherein one said substituted Gln replaces a naturally occurring Asn in the glycosylation signal corresponding to amino acids 114–116 of FIG. 1A–C herein.

16. The modified human TPA of claim 13 or claim 15 wherein one said substituted Gln replaces a naturally occurring Asn in the glycosylation signal corresponding to amino acids 181–184 of FIG. 1A–C hereof.

17. The modified human TPA of claim 16 wherein one said substituted Gln replaces a naturally occurring Asn in the glycosylation signal corresponding to amino acids 445–447 of FIG. 1A–C hereof.

18. The modified human TPA of claim 13 or claim 15 wherein one said substituted Gln replaces a naturally occurring Asn in the glycosylation signal corresponding to amino acids 445–447 of FIG. 1A–C hereof.

19. The modified human TPA of claim 13 wherein there is substituted a Gln for the Asn in three of said three glycosylation signals.

20. The modified human TPA of claim 13 wherein there is substituted a Gln for the Asn in one of said three glycosylation signals.

21. The modified human TPA of claim 13, wherein there is substituted a Gln for the Asn in two of said three glycosylation signals.

* * * * *